United States Patent [19]

Berrens

[11] Patent Number: 5,384,395
[45] Date of Patent: Jan. 24, 1995

[54] METHOD FOR THE ISOLATION OF PRIMARY-TOXIC COMPOUNDS OR ALLERGENS FROM PLANT MATERIAL

[75] Inventor: Lubertus Berrens, Utrecht, Netherlands

[73] Assignee: Laboratorios Leti S.A., Barcelona, Spain

[21] Appl. No.: 780,328

[22] Filed: Oct. 22, 1991

Related U.S. Application Data

[62] Division of Ser. No. 597,009, Oct. 16, 1990, abandoned.

[51] Int. Cl.$^6$ .............................................. A61K 35/78
[52] U.S. Cl. .................................. 530/379; 530/422; 530/427
[58] Field of Search ............... 530/379, 412, 414, 417, 530/422, 427, 370, 371, 806; 424/91, 195.1; 568/875

[56] References Cited

U.S. PATENT DOCUMENTS

| | | | |
|---|---|---|---|
| 4,146,615 | 3/1979 | Fauran et al. | 424/195.1 |
| 4,180,562 | 12/1979 | Patterson et al. | 530/379 |
| 4,234,569 | 11/1980 | Marsh | 530/379 |
| 4,605,557 | 8/1986 | Stevens et al. | 424/91 |
| 4,716,120 | 12/1987 | Tsay et al. | 424/91 |
| 4,740,371 | 4/1988 | St. Remy et al. | 424/85.8 |
| 5,013,552 | 5/1991 | Samir Amer et al. | 424/91 |

OTHER PUBLICATIONS

Ko Ito, "An Antigenic Substance, Beta–Thiyáplicín in the Steam–Distillate of the Sawdust of Thiya Standishii Carr", Med. J. Shinshu Univ. 9 (3–4), 165–170 (1964); NIOSH Abstract 00133856 and Chem. Abstr. 63, 10481a (1965).

Ault, "Techniques and Experiments for Organic Chemistry", 4th ed., Allyn and Bacon, Newton, Mass. (1983), pp. 98–99 and 328–329.

*Primary Examiner*—Michael G. Wityshyn
*Assistant Examiner*—C. Sayala
*Attorney, Agent, or Firm*—Young & Thompson

[57] ABSTRACT

Primary-toxic chemical compounds with a molecular weight of less than 12000 Daltons, which may be isolated from plant material and which are potential IgE-binding allergens causing immediate-type allergy in predisposed individuals; methods for their isolation and their use for clinical purposes.

2 Claims, 12 Drawing Sheets

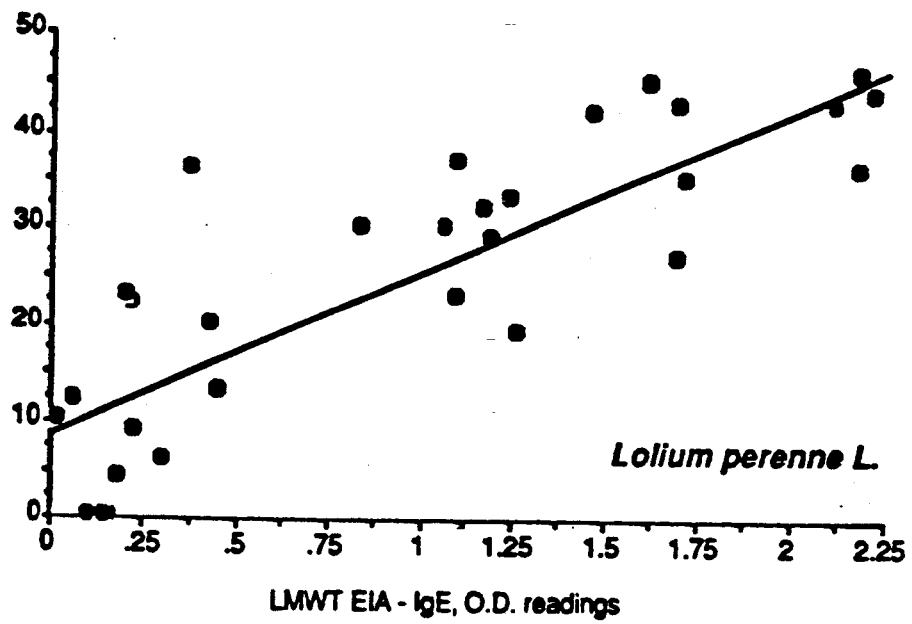

RAST Betula HMWT, %

EIA-IgE Betula LMWT

O.D. (1 cm)

wavelength, nm

METHOD FOR THE ISOLATION OF PRIMARY-TOXIC COMPOUNDS OR ALLERGENS FROM PLANT MATERIAL

This application is a division of application Ser. No. 07/597,009, filed Oct. 16, 1990, now abandoned.

The present invention relates to primary toxic chemical compounds or allergens, which may be isolated from plant material as well as methods for their preparation and application.

Hayfever is a wellknown disease which affects some 5% of the human population. The disease symptoms may be become apparent from early spring to autumn. The characteristic symptoms are recurrent coryzae and sneezing, excessive nasal secretion, swollen eyelids, light-sensitivity, all of these often in combination with widespread urticarial eruptions, bronchial spasm, asthma, and a general feeling of malaise and physical exhaustion, Patients suffering from the disease almost every year are considered to be genetically predisposed or "atopic". Since the pioneering work of Bostock and Blackley in the 19th century it has been known that such patients are allergic to the pollen of flowering grasses, trees or other plants, and that the disease symptoms become apparent under climatological conditions favouring a high pollen count of the air. Hence, the disease is known scientifically as "pollinosis". The substances in the pollen directly responsible for the disease symptoms are known as "allergens". It has become clear in recent years that patients with severe pollinosis of the upper airways often suffer from an associated intolerance to particular foodstuffs like fresh fruits, vegetables and herbs or spices of plant origin.

The chemical nature of the causative pollen allergens has been the subject of many investigations since the turn of the century. The detection of these pollen allergens thereby had to rely for a long time on the observation that the application of aqueous extracts of the pollen in or on the skin of hayfever sufferers after a 20-30 minute lag period induces a weal-and-erythema reaction; this skin response cannot be evoked in non-allergic control subjects. The reaction is attributed to the presence in blood and tissues of particular antibodies, so-called "reagins", which are known to combine with the appropriate pollen allergens and thereby initiate the local release of physiologically active biogenic amines and other cellular mediators. Reagins in the blood serum of hayfever patients may be passively transferred into the skin of non-allergic recipients; upon challange of the skin site of the normal recipient with allergen, a local weal-and-flare reaction can also be invoked: a so-called "Prausnitz-Küstner" reaction. The discovery of this passive transfer reaction provided a detection method which could subsequently be put to use for the isolation and identification of the causative allergenic molecules. When finally in 1966 these reagins were tentatively identified as the IgE-isotype of immunoglobulin antibodies it became possible to develop relatively simple serological test systems for the qualitative and quantitative evaluation of specific anti-allergen antibodies in the blood serum of allergic patients, e.g., the Radio Allergo Sorbent Test (RAST). Since that time, the RAST has found widespread application for the isolation and identification of the allergens in aqueous pollen extracts, based on the now universally accepted mechanism of an allergen-IgE triggered sequence of biochemical reactions underlying the pathology of allergic disease in man.

The above developments have led to the generally accepted viewpoint that the causative allergens in pollen and foodstuffs are proteins with a molecular weight of 25000-65000 Daltons. These allergenic proteins do not pass the usual dialysis membranes with a nominal cut-off in the range of 6000-12000 Daltons and they may therefore be separated with relative ease from the large excess of low-molecular (less than 5000 Daltons) components in allergenic extracts. The general consensus is that these low-molecular and dialysable constituents in aqueous pollen extracts are non-allergenic. Analysis of the non-dialysable allergenic portion of aqueous pollen extracts, e.g. by electrophoretic- and other proetein separation techniques subsequently showed that the allergenic components in fact are multiple. Examination of the binding pattern of electrophoretically separated pollen proteins for IgE-antibodies from the blood serum of hayfever patients revealed over 30 different allergens in extracts of individual pollen species. These IgE-binding allergens are nowadays categorized as "major" or "minor" allergens, depending on their relative concentration in the extracts and on their IgE-binding potential. Qualitatively and quantitatively, such binding patterns of physically separated pollen proteins for IgE-antibodies, or "allergograms", nevertheless differ from one hayfever patient to another.

A number of reports has in the past appeared in the scientific literature relating to the possible allergenic properties of the low-molecular weight and dialysable constituents of aqueous pollen extracts, i.e. substances with an upper limit molecular weight of about 10000 Daltons (Moore, M. B. and Moore, E. E., J. Am. Chem. Soc. 1931, 53, 2744-6; Unger, L., Cromwell, H. W., Moore, M. B., J. Allergy 1932, 3, 253-6; Johnson, M. C., Hampton, S. F., Schiele, A. W., Frankel, S., J. Allergy 1954 25, 82-3; Malley, A., Campbell, D. H., Heimlich, E. M., J. Immunol. 1964 93, 420; Attalah, N. A., Sehon A. H., Immunochemistry 1969, 6, 609-19; Girard, J. P., Berger, F., Hampai, A., Int. Arch. Allergy 1973, 45, 40-2; Lapkoff, C. B., Goodfriend, L., Int. Arch. Allergy 1974 46, 215-29; Vik, H., Elsayed, S. et al., Int. Archs. Allergy appl. Immun. 1982 68, 70). These investigations indicated that the low-molecular constituents of pollen extracts do indeed exhibit some allergenic activity, although their potency on a weight basis is a factor of 1000 less than that of the non-dialysable components. These results, together with the highly complex chemical composition of the dialyzable fraction of pollen extracts provided little impetus for pursuing these studies. Furthermore, the properties of the flavonoids and flavonoid-glycosides encountered in every pollen extract have led to considerable confusion. For these reasons, the state of the prior art is that the low-molecular weight components of pollen extracts are irrelevant in terms of their allergological and immunological contribution. In other respects these components have attracted some attention only in terms of their possible health-promoting properties, for examples tumour growth inhibitors (European patent specification 220 453; German patent specification 1,467,750; U.S. Pat. No. 3,360,437; Austrian patent specification 255,643). Similarly, peptonic products produced from whole pollen by enzymatic digestion are intended to reduce the allergenic potency of the pollen proteins, but do not reproduce the primary allergenically active IgE-binding hapten-peptide or hapten-protein complexes described in the present invention (Urbach, E., Klinishce Wochenschrift 1931; 10: 534–537; European patent specification 0 201 053).

The current viewpoint of allergens in pollen and in (cross-reacting) foodstuffs as being full proteins, however, cannot explain several wellknown clinical observations. Hayfever patients very often suffer from serious clinical symptoms even when pollen grains cannot be detected in the inhaled air, i.e. during wet seasons or in the centre of big cities. In severe cases the complaints do not remain restricted to the nasal mucosa, but develop into regular "pollen-asthma", even though the pollen grains are too bulky to reach the bronchi and in fact have never been demonstrated to penetrate into the lungs. Quite recently, observations have also been published showing that skin-reactive and IgE-binding substances characteristic of pollen allergens may occur in the ambient air even though their particle size is considerably smaller than expected for the pollen grains (Busse, W. W., Reed, C. E., Hoehne, J. H., J. Allergy Clin. Immunol. 1972, 50, 289–93; Solomon, W. R., J. Allergy Clin. Immunol. 1984, 74, 674–7). These observations have so far remained unexplained.

According to the present invention all of the above-mentioned observations may be explained. There were found primary toxic low-molecular compounds, which may be present in the form of substances having a high volatility (or vapour pressure), i.e. in the form of ethereal oil, or in the form of water-soluble glycoside derivatives of such volatile substances.

The expression "primary toxic compounds" used in the present description and claims is a generally accepted term in the field of allergology and dermatology; with said expression substances are meant which have an intrinsic property of conjugation, which means a high capacity of forming conjugates with sulfhydryl or amino groups in proteins or peptides. If said primary toxic compounds are applied onto the human skin, always an obligatory toxic effect is exerted, as can be seen from blistering, but also from sensitization finally leading to contact eczema. It should be noted that in the lastmentioned case the compounds causing such a reaction are also designated as allergens.

The volatile compounds according to the invention produce sensitization by inhalation while passing the mucosa. By conjugation they give rise to the production of protein-hapten conjugates generating an IgE-response and inducing an allergy of the immediate type.

Accordingly, the present invention relates to primary toxic chemical compounds with a molecular weight of less than 12000 Daltons, which may be isolated from plant material and which are, or may become, potential IgE-binding allergens causing immediate-type allergy in predisposed individuals. The use of such primary toxic compounds in the present invention differs markedly from previous applications of such substances, where they have been known to induce an obligatory allergic reaction of the delayed-type when applied to the skin, leading to contact eczema in every individual. (Mitchell, J. C., Dupuis, G., Geissman, T. A. Brit. J. Dermat. 1972; 87:235–240; Schulz, K. H., Garbe, I., Hausen, B. M., Simutapang, M. H., Arch. DermatolRes. 1979; 264, 275–286; International patent specification WO 84/04683). However, primary toxic substances have never before been claimed as compounds which, when applied along the mucous membranes of the upper airways, may conjugate with proteins and become haptenic determinants binding IgE-antibodies and leading to allergy of the immediate-type in predisposed, atopic individuals only.

In general, the IgE-binding activity of the compounds according to the invention is much lower than the corresponding activity of the compounds which—up to now—were assumed to be the causal allergens (i.e. proteins having a molecular weight in the order of 25000–65000 Daltons).

In particular the present invention relates to primary toxic compounds which are electrophilic and characterized by the property of conjugation with amino acids or (poly)peptides by nucleophilic addition or substitution at temperatures below 40° C.

Primary toxic substances according to the invention not being in the form of glycosides are soluble in organic solvents not miscible with water.

The compounds according to the invention may also be in the form of water-soluble glycosides. Such glycosides are e.g. derivatives of aliphatic or alicyclic terpenoid compounds which have been attached to the carbohydrate by means of an exocyclic methylene group.

It should be noted that the primary toxic compounds or allergens according to the invention belong in general to the group of mono or sesqui terpenoids having one or more reactive carbonyl, epoxy or vinyl groups, or to the group of substituted benzoquinones, such as ortho or para benzoquinones.

The present invention also relates to methods for the isolation of primary toxic compounds or allergens from plant material, e.g. from the pollen of grasses, trees, shrubs and other plants as well as from foodstuffs, which method is characterized in that compounds having a molecular weight of less than 12000 are separated from said plant material. For identification of the compounds aimed at, use can be made of the IgE-binding activity.

According to a preferred embodiment the primary toxic chemical compounds according to the invention are isolated on the basis of their capacity for binding specific IgE-antibodies.

According to a further embodiment of the method of the invention an aqueous extract of plant material is submitted to passage through a dialysis membrane or ultrafilter, or to molecular sieving. In such an embodiment a separation into a high molecular fraction (molecular weight above 12000 Daltons) and a low molecular fraction (molecular weight below 12000 Daltons) is performed. Then, the fraction of the plant material containing no substances having a molecular weight above 12000 may be extracted with an organic solvent, water or a buffer solution, preferably having a pH-value of 6–7.5.

It is also possible to subject plant material to steam distillation, optionally after removal of compounds having a molecular weight above 12000. Such a procedure is preferred in the case of plant material not being subjected to drying or defatting.

It is preferred to extract plant material from which any compounds having a molecular weight above 12000 have been removed, with a non-water-miscible organic solvent, being in particular volatile, followed by steam distillation of the extract obtained. In such a case it is possible to hydrolyze the glycosides in the plant material before or during the steam distillation, e.g. in alkaline aqueous solutions having in particular a pH-value of 9–11. The steam distillate will contain the primary toxic compounds according to the invention which may be recovered by extraction with an organic solvent not miscible with water.

It will be understood that the abovementioned treatments according to the invention—with the exception of the steam distillation—will be performed as much as possible at low temperature, e.g. below 10° C., in order to avoid decomposition of the compounds aimed at.

The present invention also relates to the use of the primary toxic compounds or allergens obtainable according to the methods of the present invention. For instance, said compounds may be used for preparing protein conjugates having allergenic properties, in which case said compounds are coupled to a carrier protein. A suitable carrier protein is non-allergenic and has a molecular weight of at least 20000 Daltons. In addition, the protein molecule contains at least two cysteine amino acid residues. The compounds according to the invention are coupled to the carrier protein according to methods known in the art. Preferably, a coupling or conjugation is carried out by interaction between the components in an aqueous medium, generally a solution, emulsion, or dispersion at a temperature of 20°-40° C. and a pH-value of 8.5-11.

It will be understood that the compounds according to the invention, or the compositions which may be prepared according to the method of the invention, may be used for the same purposes as the compounds which have been considered as allergenics up to now. This means that the present compounds may be used in e.g. test kits or desensibilisation compositions.

Consequently, the present invention also relates to the use of the present compounds for the preparation of compositions suited for the treatment of allergic disorders and to the use for purposes of analysis, diagnosis and standardization.

It will be evident from the above that the present invention provides an integral approach by describing procedures for the isolation from pollen and foods of low-molecular weight substances which are primarily toxic to genetically predisposed atopic people. Such substances may occur both in the form of highly volatile organic compounds or as their water-soluble and relatively low-molecular glycosidic conjugates. The primary toxicity of the aglycones is due to their strong tendency of forming chemical conjuages with thiol- or amino-groups in proteins or peptides. After this conjugation reaction the now chemically bonded compounds may be structurally recognized by the immunological system of hayfever patients as "haptenic" side-chains affixed to protein carrier molecules. When the protein conjugates comprises at least two or more identical foreign haptenic structures, they become increasingly potent as regular high-molecular weight IgE-binding allergens causing allergy of the immediate type.

BRIEF DESCRIPTION OF DRAWINGS

FIG. 1. Scatter diagram for the quantitative relation between IgE-antibodies to *Lolium perenne* allergens, evaluated against the protein allergens HMWT by means of the RAST-method, and against the total dialysable fraction LMWT by means of enzyme immunoassay. Number of sera from pollinosis patients $N=30$, Spearman rank coefficient of correlation $r(S)=0.83$, $P<0.00002$. Regression line: $y=16.8x+8.8$.

FIG. 2. Elution pattern of *Lolium perenne* pollen LMWT, 2.5 ml in distilled water from a $90\times 1.4$ cm ($\phi$) column of Sephadex G25 Fine. Fractions of 100 drops were collected automatically, with continuous monitoring of 280 nm light absorption. After the separation, fractions were combined into 4 separated Pools as indicated in the figure.

μg/ml, the hygroscopic Pool II in 1:250 dilution. The allergenically most potent fraction Pool I contains only traces of flavonoids.

Figure 14:
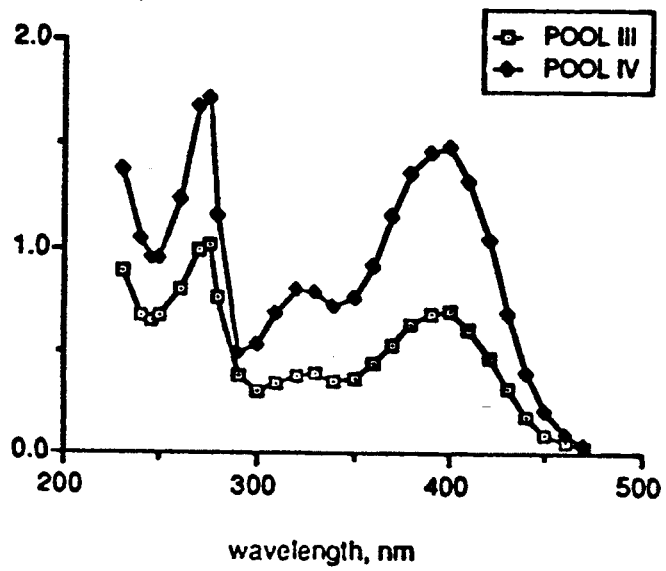

FIG. 14. Ultraviolet absorption spectra in 0.1M NaHCO$_3$ pH 9.4 of the allergenically inactive LMWT-subfractions III and IV from *Parietaria judaica* pollen, both at 40 μg/ml. These inactive fractions contained flavonoids or flavonoid-glycosides of the quercitine type.

Figure 15:
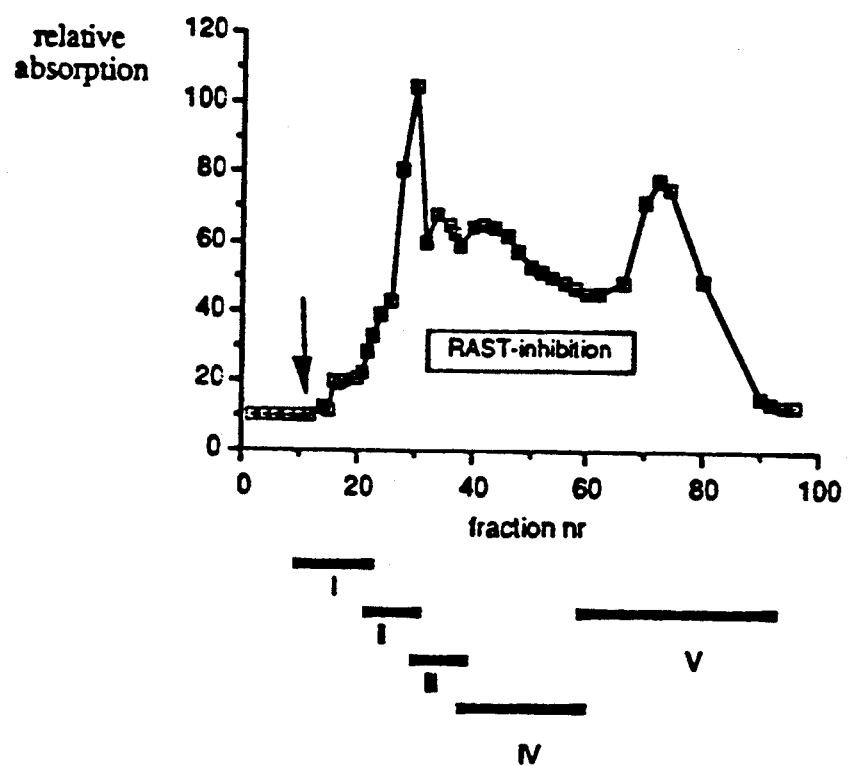

FIG. 15. Elution pattern of *Betula alba* LMWT, 2 ml concentrated solution in water, percolated through a 85×1.4 cm (φ) column of Sephadex G25 Fine in water. Fraction size 5 ml, relative absorption monitoring at 280 nm. The collected fractions from 3 separate runs were combined into 5 Pools. The arrow indicates the elution point of the molecular weight marker Blue Dextran. The effluent position of the most potent IgE-binding components reveals a lower molecular size (approx. 1000–3000 Daltons) than the LMWT-fractions in the previous Examples.

Figure 16:
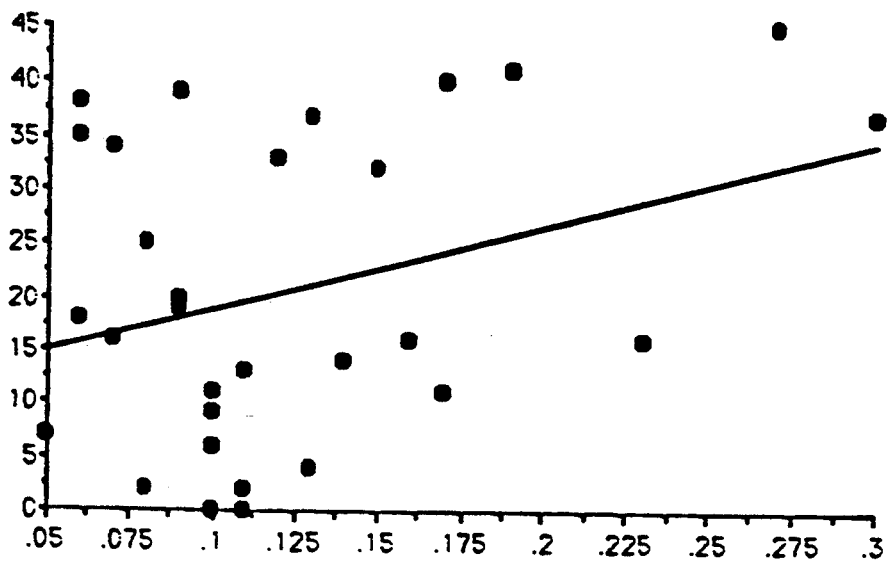

FIG. 16. Scatter diagram for the quantitative relationship between the IgE-antibodies against *Betula alba* allergens measured against the protein allergens HMWT by means of the RAST-method and against the total dialysable fraction LMWT by means of enzyme immunoassay. Number of serum samples from pollinosis patients N=30, Spearman rank coefficient of correlation r(S)=0.83, P<0.175 (not significant). Linear regression line: y=78.4x+11.0.

Figure 17:
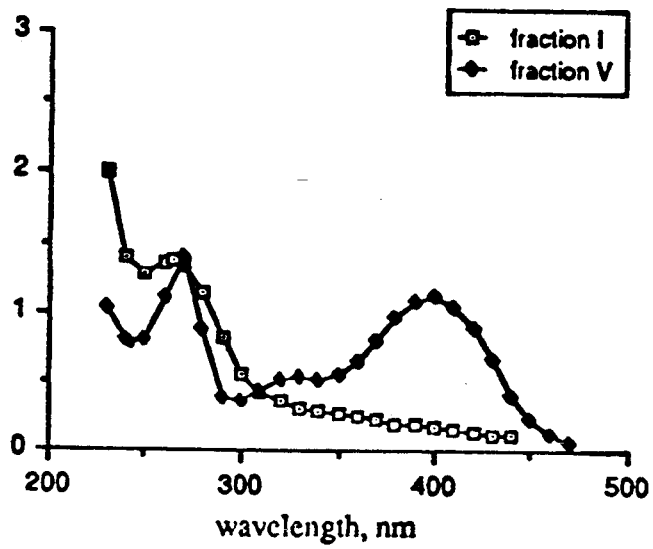

FIG. 17. Inhibition of IgE-binding from the pooled blood sera of 4 patients with an isolated allergy to *Betula alba* pollen (RAST undiluted serum pool=38.5%) by the major allergens HMWT extracted from untreated and ether-defatted pollen grains, respectively, and by the dialysable components LMWT and its 5 subfractions. The inhibitory ratio was HMWT non-def.: HMWT:I:II:III:IV:V=1:3:∞:10000:17783:7079:∞. By the previous removal with ether of the "pollen-oil" (or "oleoresin"), the allergenic potency of the water-soluble major allergens is decreased by a factor 3.

Figure 18:
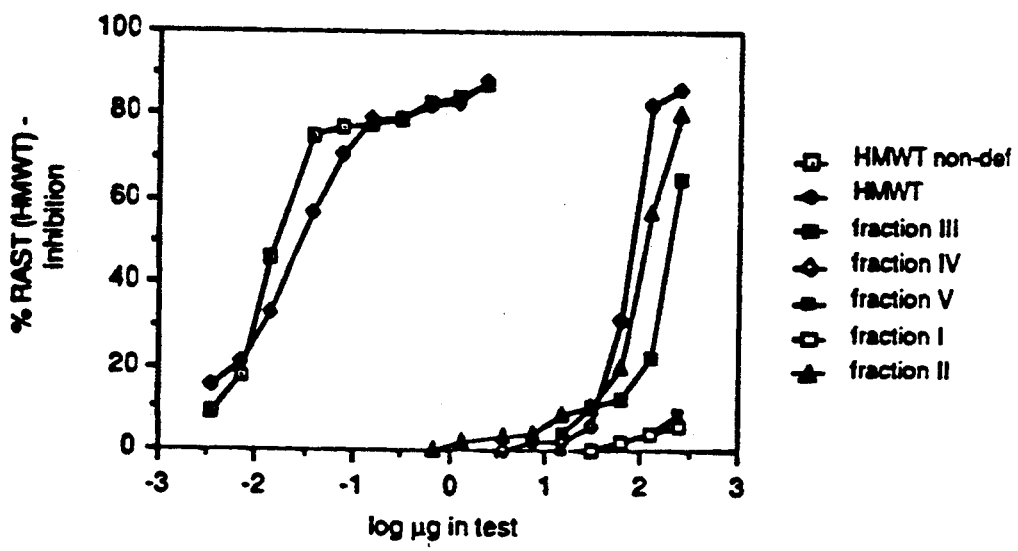

FIG. 18. Ultraviolet absorption spectra in 0.1M NaHCO$_3$ pH9.4 of the allergenically inactive subfractions I (dilution 1:100) and V (0.04 mg/ml) from *Betula alba* LMWT. The fractions richest in flavonoids (absorption maximum at 400 nm) have the lowest molecular size.

Figure 19:
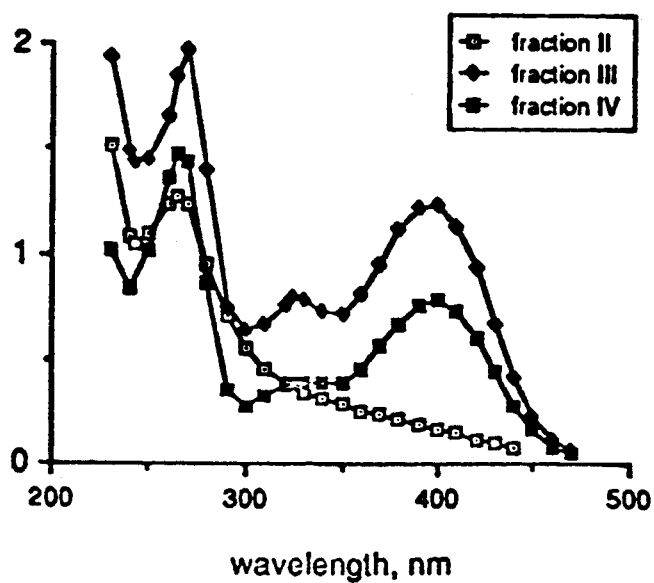

FIG. 19. Ultraviolet absorption spectra in 0.1M NaHCO$_3$ pH 9.4 of the allergenically active subfractions II (dilution 1:100), III (0.1 mg/ml) and IV (0.5 mg/ml) from *Betula alba*. Comparison of the spectra with the RAST-inhibition data from FIG. 17 shows that the flavonoid constituents do not contribute to allergenic potency.

FIG. 20.

Ultraviolet absorption spectra in 0.1M phosphate buffer pH 7+0.9% NaCl (PBS) of the major allergenic fractions HMWT from *Betula alba* LMWT (0.05%) and *Corylus avellana* (0.02%) in relation to the semi-synthetic "birch-pollen" HMWT preparation (0.1%) produced from birch-pollen LMWT (spectrum in 1:100 dilution) and Corylus HMWT. These spectra show that the flavonoid constituents are non-allergenic and low-molecular weight, with a strong tendency to adsorb to the high-molecular weight components. Like the aqueous stream distillate from LMWT at pH 10, the semi-synthetic allergen contains no flavonoids.

Figure 21:
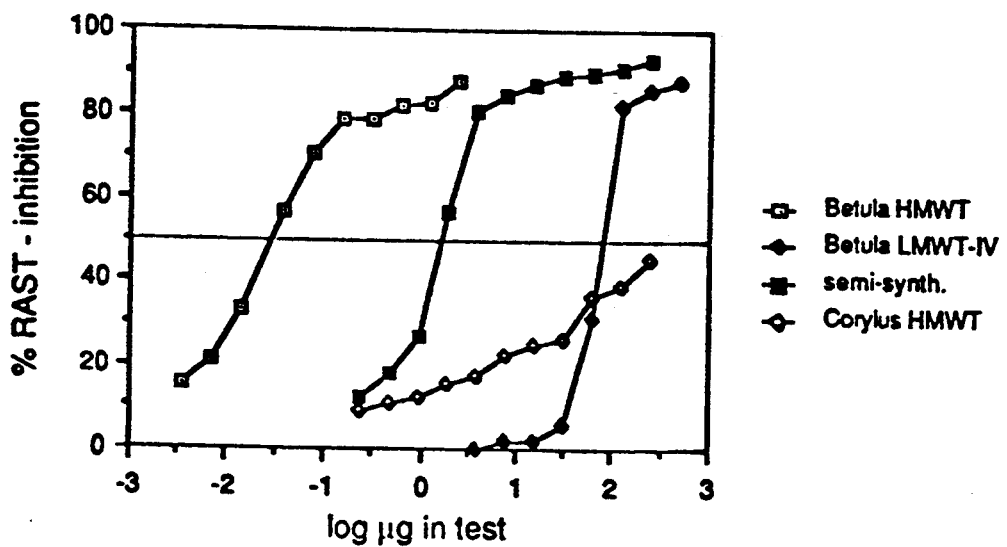

FIG. 21. Inhibition of IgE-binding from the pooled blood sera of 4 patients with pollinosis due to *Betula alba* (RAST undiluted serum pool=38.5%) by the major allergens HMWT from *Betula alba* and *Corylus avellana* pollen, as well as by the dialysable allergenic Pool IV from birch pollen LMWT and by a semi-synthethic HMWT allergenic preparation produced from the low-molecular weight birch pollen components and the high-molecular weight carrier proteins from *Corylus avellana*. The inhibitory ratio was Betula HMWT:semi-synthetic product:Betula LMWT-IV: Corylus HMWT=1:47:2360:10541.

Figure 22:
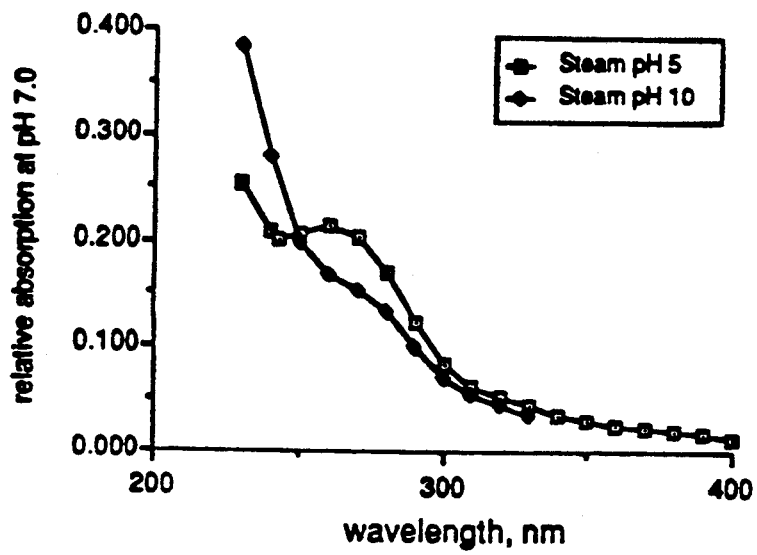

FIG. 22. Ultraviolet absorption spectra in water of the steam distillates from the LMWT preparation of *Betula alba*, volatilized from solution at pH 5 or pH 10, respectively. Concentrations unknown. The steam distillates contain no flavonoids, but (carbonyl containing) compounds absorbing at 260–270 nm.

Figure 23:
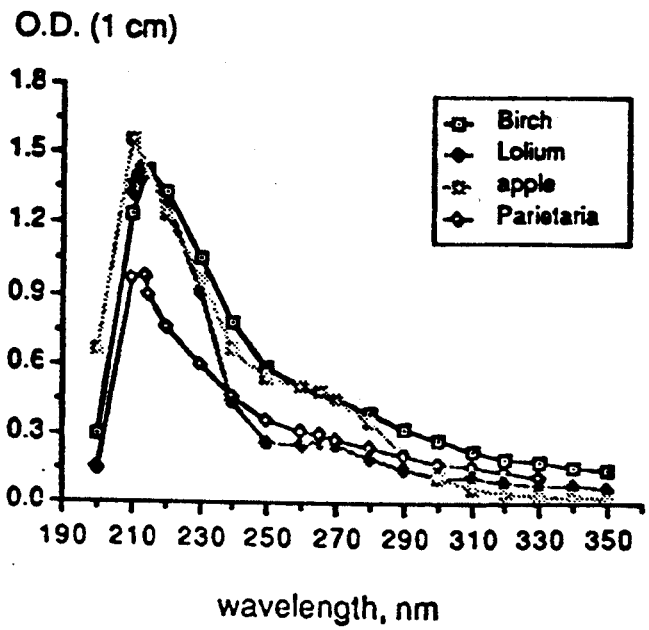

FIG. 23. Ultraviolet absorption in 96% ethanol of the ether-extracted steam distillate of the dry and untreated pollen grains of *Betula alba*, *Parietaria judaica* and *Lolium perenne*, and of aqueous fresh apple fruit extract (*Pinus malus* L., var. Granny Smith). Concentrations unknown. All spectra feature maxima in the very short wavelength range of 200–220 nm, in agreement with their possible identity as (mono- or sesqui-) terpenoid structures.

The invention is illustrated in the Examples, which also describe procedures for the isolation of the primary-toxic reaction partners. The invention demonstrates in Examples V and VI the chemical conjugation of isolated hapten-precursors to proteins, thus allowing the preparation of semi-synthetic high-molecular weight IgE-binding allergens that can be used for laboratory and clinical purposes.

In Example I a procedure is described for defatting and extracting the pollen of the grass *Lolium perenne* L. with an aqueous buffer solution. The separation into dialysable (LMWT) and non-dialysable components is reported, together with the use of the HMWT-portion for demonstrating specific IgE-antibodies in the blood-serum of hayfever patients. In the case of *Lolium perenne* the unfractionated LMWT-fraction still encompasses components that can be used for the quantitative determination of IgE-antibodies, e.g., by enzyme immunoassay. Separation of the LMWT-portion by percoluation through molecular sieving columns demonstrates that these particular IgE-binding substances—which are about 500–1000×less potent than the HMWT-components—have a molecular size of 5000–10000 Daltons. The ultraviolet absorption spectra of these fractions show them to be composed of peptide-carbohydrate and/or peptide-pigment (non-flavonoid) conjugates.

In the case of the pollen of the weed *Artemisia vulgaris* L. in Example II the molecular size of the individual IgE-binding LMWT components is of the same order of magnitude as that of the LMWT constituents of *Lolium perenne* L. However, the Artemisia LMWT preparations display a higher concentration of water-soluble flavonoid-conjugates devoid of allergenic activity. The active LMWT-fractions are hygroscopic and contain carbohydrate as well as conjugated UV-absorbing non-flavonoid chromophores. By way of an "immunoblotting-inhibition technique" it can be demonstrated that the most potent LMWT-fractions contain structural chemical determinants which are being recognized by all IgE-antibodies against the HMWT-allergens. This result clearly shows that these HMWT-allergens are not "multiple" because of immunologically different antigenic protein structures, but because these distinct proteins are conjugated in different proportion to the same low-molecular weight chemical primary-toxic chemical structures.

In Example III the LMWT components are isolated and separated into fractions of the pollen of the Mediterranean weed *Parietaria judaica* L. Hypersensitivity to this particular pollen clinically clearly features both allergic and toxic symptoms. The pollen is very difficult to obtain in pure form and is usually mixed with some 25% of other plant parts. The extracts are therefore rich in pigments, especially chlorophyll. The isolation and analytical procedure shows that these pigments, bound glycosidically or not, are allergenically inactive. This is also demonstrated in Example IV, which details the same procedure for the pollen of *Betula alba*, which likewise is rich in pigments. In the Betula situation, the active dialysable components are of lower molecular size than found in the foregoing Examples. In conjunction with the negative results obtained with *Betula alba* LMWT in enzyme immunoassays for IgE-antibodies these data show that allergenically active allergens must at least be bivalent in terms of the number of IgE-binding haptens per carrier molecule. The procedure of Example IV also demonstrates that the most potent allergens are obtained by omitting the defatting step with organic solvent prior to aqueous extraction, indicating that the reactive haptenic precursor compounds are concentrated in the "pollen-oil". Example V describes a procedure whereby these hapten-precursors are released as (volatile) organic compounds in free and reactive form by treatment in alkaline medium. By reacting the thus released "toxins" with allergenically virtually inactive proteins from the pollen of the hazel tree *Corylus avellana* L., which is botanically closely related to the birch tree, a semi-synthetic high-molecular weight multivalent analogue of the potent birch pollen allergen is prepared. In Example VI a procedure is given for obtaining these reactive toxins directly from the untreated pollen grains or from the concentrated dialysable components LMWT of crude aqueous extracts by steam distillation. Their possible identity as mono-o or sesqui-terpenoids is indicated.

EXAMPLE I

A quantity of 100 grams of microscopically pure and dry pollen of *Lolium perenne* (Biopol Laboratories, California, USA) was percolated in a Soxhlet apparatus with dry diethylether until the extraction fluid became colourless (about 6 hours). The ether-phase was taken to dryness in a stream of cold air and the residue was dissolved in 96% ethylalcohol. Dry pollen preparations generally contain 5-10% by weight of substances soluble in organic solvents such as ethylether, petrolether or ethylacetate. The defatted pollen-residue was dried in air, weighed, and extracted at room temperature with 500 ml distilled water for 2 h with stirring. After centrifugation, the residue was re-extracted in similar fashion. The combined aqueous extracts were then dialyzed for 4 h at +4° C. (Visking membrane, nominal cut-off 10000 Daltons) against 2 listers of distilled water. The first dialysate (outer liquid) was lyophilized and produced a hygroscopic substance, which was taken up in 50 ml distilled water and was stored as LMWT-product at −40° C. The retentate (inner liquid) was dialyzed for a further 24 h against repeated changes of water and was finally freezedried to give the HMWT-product. The yield of HMWT for pollens of the Gramineae family usually is in the order of 8-10%.

For the determination of IgE-antibodies against the LMWT components the (flat-bottom) wells of polystyrene microtiter plates (Dynatech) were treated with LMWT-preparations prediluted with 0.1M NaNCO$_3$ to an optical density at 275 nm of 1.0 in 1 cm quartz cuvettes; the dilution factor was in the order of 20-35. After drying the LMWT-coated wells, the plates were incubated with dilute patient's serum and in the next step with peroxidase-labellwed goat antiserum to human IgE in 1:400 dilution (TAGO Laboratories, California, USA). Colour development was finally achieved with a peroxidase substrate like o-phenylene diamine or tetramethylbenzidine. Quantitative IgE-binding by LMWT or its subfractions evaluated by this technique represents a diagnostic method correlating quite well with the results for IgE-binding against the HMWT-components obtained with the classical RAST-method (FIG. 1).

Figure 4:
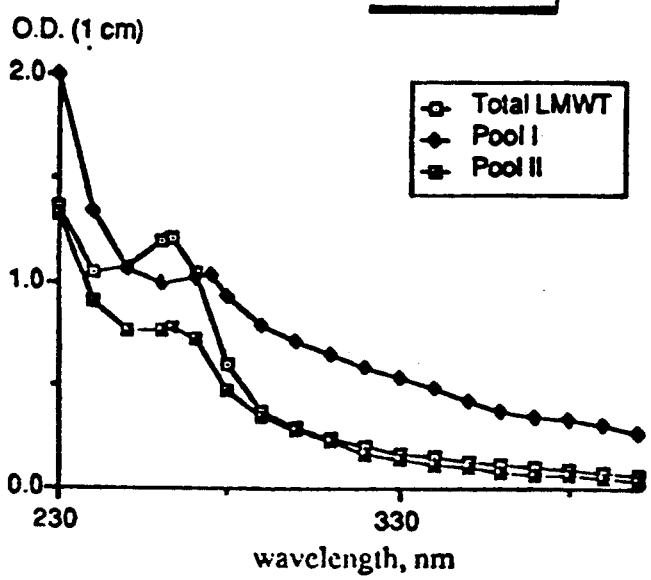
FIG. 4. Ultraviolet absorption spectra in 0.1M NaHCO$_3$ pH 9.4 of the active low-molecular IgE-binding LMWT-fractions from *Lolium perenne* SI and SII in relation to the starting material. LMWT in 1:100 dilution, Pool I in 0.1% w/v solution, Pool II in 1:100 dilution. Increased absorption at over 300 nm is not associated with an increased IgE-binding capacity.
Figure 5:
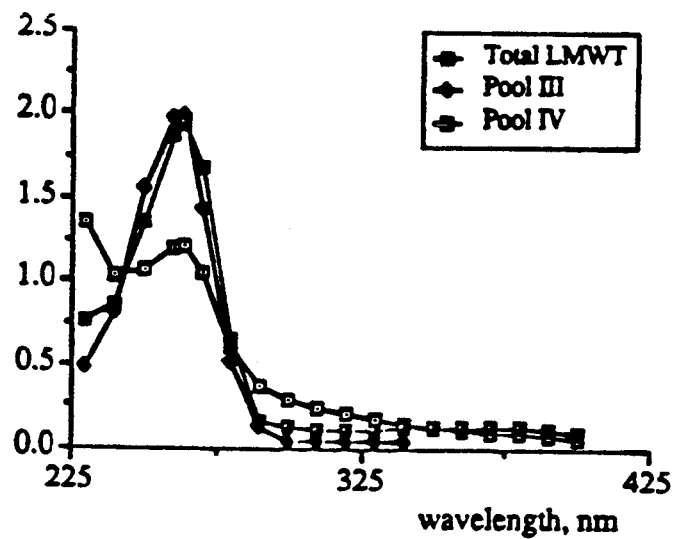
FIG. 5. Ultraviolet absorption spectra of the allergenically inactive LMWT-fractions III (50 $\mu g$/ml) and IV (100 $\mu g$/ml) of *Lolium perenne* in 0.01M NaHCO$_3$ pH 9.4. The absorption-maximum of both fractions is at 260-262 nm: E(1%, 1 cm) fraction III=400, fraction IV=193.

For the separation of the LMWT-components a volume of 2.5 ml LMWT-concentrate was percolated through a molecular sieving column of Sephadex G25 (Pharmacia AB, Uppsala, Sweden) suspended in distilled water. The column was then eluted with distilled water and the effluent fluid was collected in separate fractions. For preparative purposes the same column may be used for repeated LMWT-applications. In this Example the effluent column fractions were combined into 4 pools on the basis of the elution diagram shown in FIG. 2, yielding Pool I (colourless)=11 mg, Pool II (yellow, hygroscopic, taken up in 5 ml dist. water), Pool III (yellow)=3 mg, Pool IV (yellow)=0.5 mg. The ultraviolet absorption spectra of these low-molecular weight pools are represented in FIGS. 4 and 5.

Figure 3:
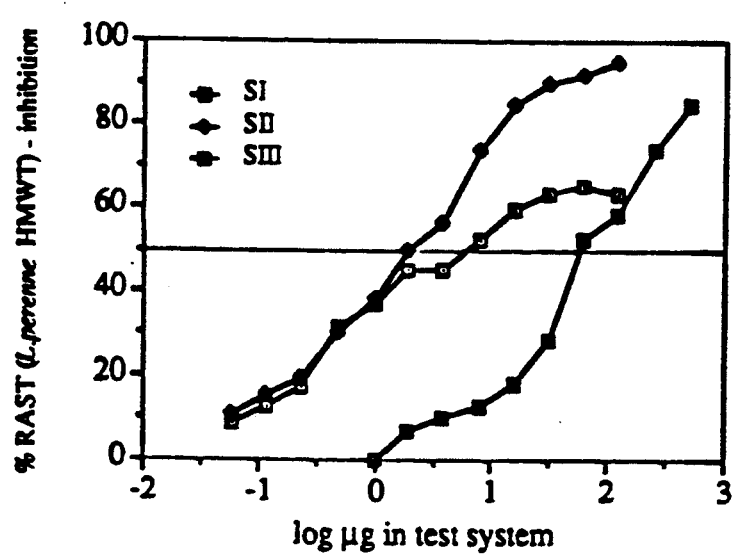
FIG. 3. Inhibition of IgE-binding in the blood serum of a pollinosis patient by pre-incubation with the separated LMWT fractions SI, SII, and SIII from *Lolium perenne*. For each fraction the inhibitory capacity is expressed in $\mu g$ for 50% RAST-inhibition. The inhibitory ratio was SII:SI:SIII=1:3.6:31.7.

The IgE-binding capacity of LMWT and its subfractions was established by way of the radioallergosorbent test (RAST); the results are shown in FIG. 3.

EXAMPLE II

Figure 6:
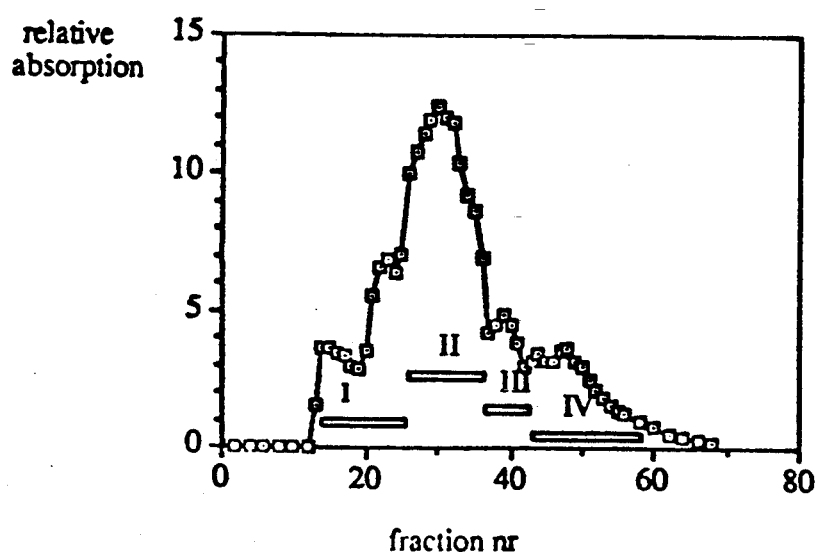
FIG. 6. Elution pattern of *Artemisia vulgaris* LMWT, 2 ml concentrated solution in water, percolated through a $80\times 1$ cm ($\phi$) column of Sephadex G25 Fine in water. Effluent fraction-volume 5 ml, relative absorption monitored at 280 nm. The isolated fractions of three separate runs were combined into 4 Pools as indicated.
Figure 7:
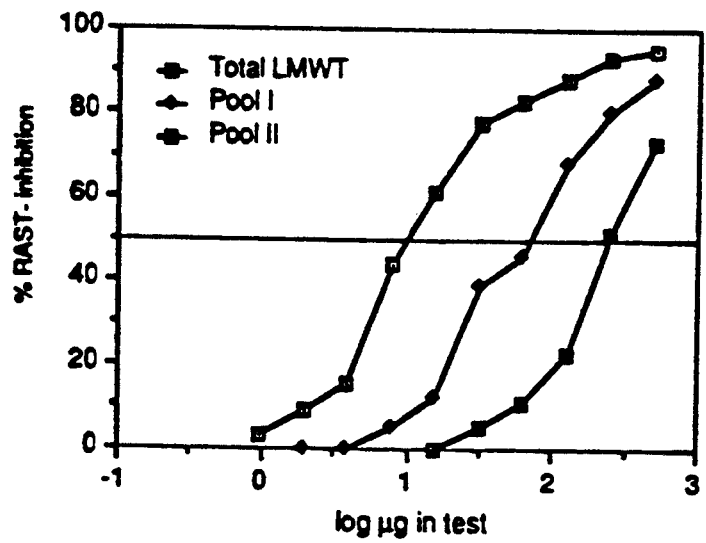
FIG. 7. Inhibition of IgE-binding in serum sample #880528 of a patient with monovalent pollinosis due to *Artemisia vulgris* (RAST undiluted serum=41%) by LMWT and its subfractions I and II in a dilution series of a stock solution at 10 mg/ml, 50 $\mu l$ per test; fractions III and IV were completely inactive. The IgE-binding ratio was LMWT: Pool I: Pool II=1:6.3:25.1.
Figure 8:
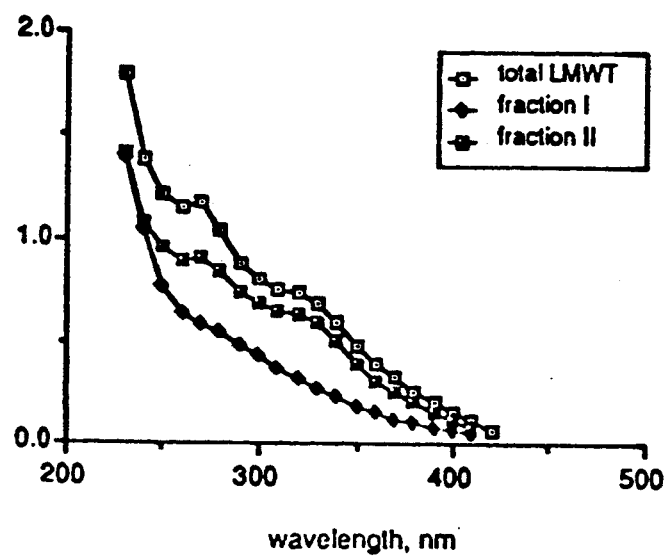
FIG. 8. Ultraviolet absorption spectra of the IgE-binding fractions LMWT from *Artemisia vulgaris* pollen and the subfractions Pool I and Pool II at pH 7.0 in distilled water; LMWT in 1:200 dilution, Pool I at 1 mg/ml, and Pool II in 1:500 dilution. Fraction (I) from LMWT with the least pronounced spectrum had the highest IgE-binding capacity.
Figure 9:
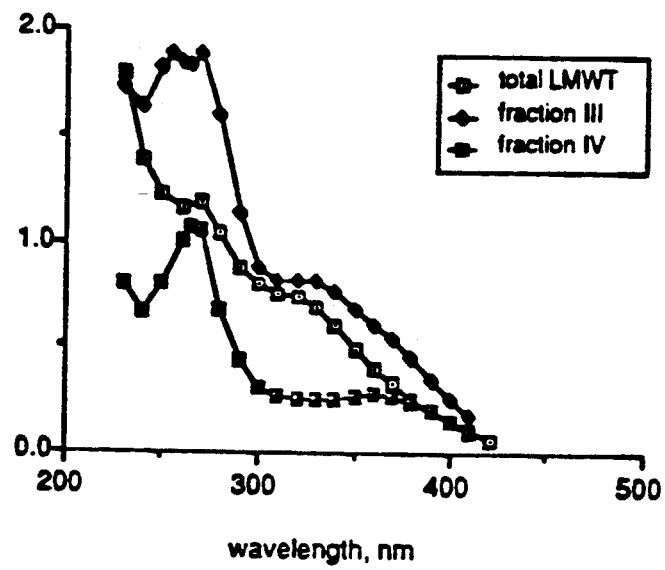
FIG. 9. Ultraviolet absorption spectra in distilled water of the allergenically inactive subfractions III (0.1 mg/ml) and IV (0.05 mg/ml) from *Artemisia vulgaris* LMWT. These fractions are rich in flavonoid components (absorption maxima at 325-360 nm).

A 25 gram sample of dry pollen of *Artemisia vulgaris* (Greer Laboratories, Lenoir, N.C., USA, lot Nr. 85 Y 47 - 7B) was defatted with diethylether, extracted with distilled water and separated into HMWT and LMWT fractions as described in Example I. The yield of HMWT was 8.4% from the dry undefatted pollen. The LMWT fraction was then separated further by molecular sieving on a column of Sephadex G25 Fine in distilled water as described in Example I. The elution diagram is shown in FIG. 6. The overall yield of 3 runs of 2 ml LMWT each was: Pool I=133 mg, Pool II (hydroscopic, taken up in 2 ml distilled water), Pool III=5.1 mg, Pool IV=4.5 mg. The IgE-binding capacity was evaluated by RAST-inhibition and is depicted quantitatively in FIG. 7. The binding of specific IgE-antibodies was also demonstrated as follows. A 250 μl serum sample of a patient with a high level of circulating IgE-antibody to the HMWT-allergens of *Artemisia vulgaris* (#880528, RAST-value in indiluted serum 41%). was pre-incubated with 50 μl of a 1% solution of the Artemisia-LMWT sufractions I, II, III and IV, respectively. The HMWT fraction in 4% solution was subjected to isoelectric focusing in polyacrylamide gel, followed by "Western blotting" (i.e. electrophoretic transfer) onto a nitrocellulose sheet. The nitrocellulose print, after treatment with human serum albumin, was then soaked for 2 h with the serum-LMWT mixtures in 1:10 dilution. The sheet was next treated with peroxidase-labelled antiserum against human IgE, and finally developed for colour with a peroxidase substrate. These experiments unequivocally demonstrated that the IgE-antibodies against each and every high-molecular weight Artemisia allergen separated by isoelectric focusing were blocked by the LMWT-subfractions, whereby the blocking capacities showed the same ratios as in the RAST-inhibition assay. Subfractions I and II therefore contain antigenic determinants which occur as haptens on each and every high-molecular weight constituent allergen. The ultraviolet absorption spectra of the IgE-binding fractions I and II, and of the non-allergenic fractions III and IV are shown in FIGS. 8 and 9, respectively.

EXAMPLE III

Figure 10:
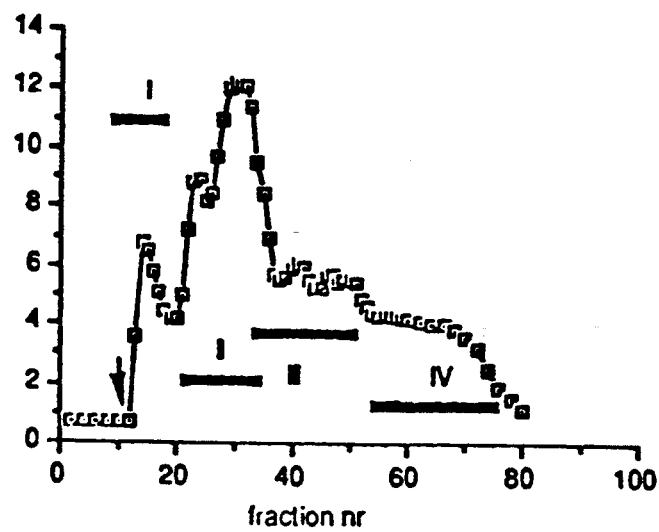
FIG. 10. Elution pattern of *Prietaria judaica* LMWT, 1.5 ml concentrated solution in water, percolated through a $85\times 1.4$ cm ($\phi$) column of Sephadex G25 Fine in water. Fraction size 5 ml, relative absorption at 280 nm. Combined fractions from 3 separate runs were pooled as indicated.

Dry pollen of the plant *Parietaria judaica* (Allergon AB, Sweden) was extracted and separated into fractions as described in the procedure of Example I. The yield of HMWT-product was 2.5–3.5% w/w, dependent on the batch. The separation of the LMWT-fraction into 4 subfractions is shown graphically in FIG. 10. The total yield of the different Pools from 3 separate runs of 1.5 ml LMWT-solution each was: Pool I (brown, 13.8 mg), Pool II (brown, hygroscopic, taken up in 7 ml of water after freezedrying), Pool III (yellow, 7.2 mg), Pool IV (yellow, 6.9 mg).

Figure 11:
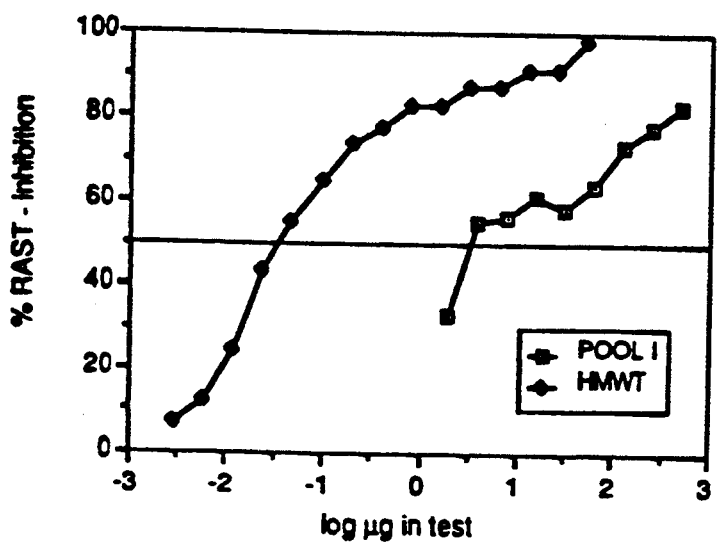
FIG. 11. Inhibition of IgE-binding from a pool of blood sera of 4 Spanish patients with monovalent pollinosis due to *Parietaria judaica* (RAST undiluted serum pool=16%), by the non-dialysable allergens HMWT and the LMWT-subfraction I. The inhibitory ratio was HMWT:Pool I=1:105.
Figure 12:
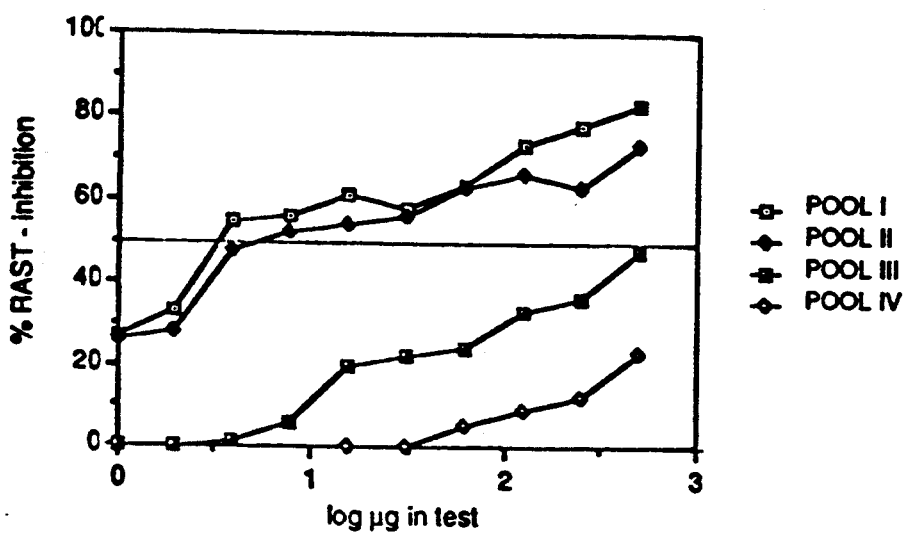
FIG. 12. Inhibition of IgE-binding from a pool of blood sera of 4 Spanish patients with monovalent pollinosis due to *Parietaria judaica* (RAST undiluted serum pool=16%) by the LMWT-subfractions I through IV. The inhibitory ratio was I:II:III:IV=1:1.7:167:500.
Figure 13:
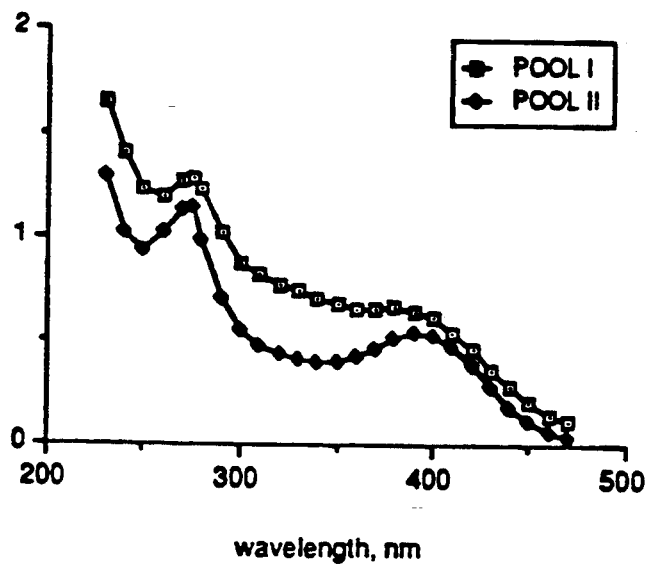
FIG. 13. Ultraviolet absorption spectra of the IgE-binding LMWT-subfractions I and II from *Parietaria judaica* pollen in 0.1M NaHCO$_3$ pH 9.4; Pool I at 200

The results of the IgE-binding assays by RAST-inhibition in relation to the HMWT-product are shown in FIGS. 11 and 12. The ultraviolet absorption spectra of the active subfractions I and II, and of the inactive fractions III and IV are given in FIGS. 13 and 14. The structural interpretation of the spectra follows from Table 1.

A) in a yield of 1.95% w/w. At the same time, a 1 gram sample was first defatted with ether and then extracted and dialyzed to obtain a HMWT-product in a yield of 1.70% (Product B). Tested on an equal weight basis in RAST-inhibition the non-defatted HMWT product A provide to be a factor of 3 more potent than its ether-defatted counterpart product B (FIG. 17). This demonstrates the presence in the pollen-oleoresin portion of ether-soluble compounds with the chemical structure of the allergenically active haptenic epitopes also occurring on the classical high-molecular weight water-soluble pollen proteins. These chemically relative compounds can be adsorbed with active charcoal, from which they may be eluted with ethylalcohol.

In contrast to the low-molecular IgE-binding component of *Lolium perrene* in Example I, the LMWT-solutions of *Betula alba* proved to be unsuited for coating to polystyrene plates for subsequent diagnostic IgE-determination (FIG. 16). Comparison of the data of FIGS. 15 and 16 with those of FIGS. 1 and 2 shows that this unsuitability is due to the appreciably lower molecular size of the most active Betula LMWT-fractions. Hence, the most powerful LMWT-components of Lolium most likely represent multi- or at least bivalent (glyco-) peptides already carrying conjugated haptens from the pollen ethereal oil, whereas the IgE-binding LMWT-components from Betula probably are monovalent water-soluble glycosides of haptenic precursor molecules and/or hapten/amino acid conjugates. Such low-molecular conjugates have a strong tendency for physical adsorption to proteins and can therefore only be eliminated during prolonged dialysis, preferably from

TABLE 1

Extinction coefficients at pH 9.4 of the low-molecular weight components from aqueous extracts of *Parietaria judaica* pollen in relation to some crystalline flavonoids and glycosides.

| Fraction | E (1%,1 cm) 275 | E (1%, 1 cm) 325 | E (1%, 1 cm) 395 | E395/325 | E395/275 |
|---|---|---|---|---|---|
| Pool I | 64.3 | 37.5 | 32.5 | 0.87 | 0.51 |
| Pool II | n.d. | n.d. | n.d. | 1.35 | 0.46 |
| Pool III | 255 | 145 | 225 | 1.55 | 0.88 |
| Pool IV | 430 | 203.8 | 372.5 | 1.83 | 1.15 |
| RUTIN | 1620 | 630 | 1340 | 2.13 | 0.83 |
| APIGENIN | 850 | 450 | 970 | 2.15 | 1.14 |
| RHOIFOLIN | 74 | | 182 | | 2.46 |

EXAMPLE IV

A quantity of 25 grams of dried pollen of the birch tree (*Betula alba* L., Greer Laboratories Lenoir, N.C., USA, batch Nr. 46Y80-4) was defatted with diethylether and then extracted twice with 200 ml of distilled water according to the procedure of Example I. The extract was separated into HMWT and LMWT products (yield of HMWT: 2.3% w/w). The aqueous LMWT-fraction was then divided into 5 subfractions according to the procedure of Example I; the separation pattern is shown in FIG. 15. From a total of 6 ml concentrated LMWT-solution the recoveries were: Pool I (fractions 14–24, colourless and hygroscopic, taken up in 5 ml of water after freezedrying), Pool II (fractions 24–31, orange, hygroscopic, taken up in 3 ml of water after freezedrying), Pool III (fractions 33–38, yellow, 4.8 mg), Pool IV (fractions 39–57, yellow, 13.5 mg), Pool V (fractions 58–90, yellow, 21.5 mg).

In a separate experiment 1 gram of birch pollen from the same batch was extracted with distilled water without previous defatting with ether; the aqueous extract was directly submitted to dialysis and lyophilization of the retentate to obtain a HMWT-preparation (Product weakly acid medium. These results were sustained by the accidental observation of a birch pollen sensitive patient who in the course of immunotherapeutic treatment received a subcutaneous injection of a birch pollen HMWT preparation that had been dialysed for only 4 h; the patient experienced a life-threatening anaphylactic shock reaction within 15 minutes. The subsequent administration one week later of the same extract subjected to continued dialysis for 48 h produced no untoward response, however. Hence, unfractionated aqueous pollen extracts not only comprise IgE-binding high-and-low-molecular weight allergens, but also potent low-molecular weight toxins, which may be structurally related and which occur unconjugated in the pollen oil as well as in the form of water-soluble natural glycosides.

The IgE-binding capacity of the LMWT-fractions is shown in FIG. 17. The ultraviolet absorption spectra of the inactive components I and V and of the active subfractions II–IV are drawn in FIGS. 18 and 19, respectively. Taken together with the analytical data of Table 2 these results allow the conclusion that the flavonoid pigments are allergologically irrelevant.

TABLE 2

| Fraction | Extinction coefficients at pH 9.4 of the low-molecular weight components in aqueous extracts of *Betula alba* pollen. | | | | |
|---|---|---|---|---|---|
| | E (1%, 1 cm) 270 | E (1%, 1 cm) 325 | E (1%, 1 cm) 400 | E400/325 | E270/400 |
| LMWT | n.d. | n.d. | n.d. | 1.68 | 1.90 |
| I | n.d. | n.d. | n.d. | n.d. | n.d. |
| II | n.d. | n.d. | n.d. | n.d. | n.d. |
| III | 198 | 90 | 124 | 1.38 | 1.60 |
| IV | 294 | 78 | 157 | 2.00 | 1.87 |
| V | 348 | 140 | 280 | 2.00 | 1.24 |

EXAMPLE V

ON the basis of the foregoing Examples a synthetic "birch-pollen allergen" was prepared. The HMWT components for the pollen of the hazelnut tree (*Corylus avellana* L., Greer Laboratories, Lenoir, N.C., USA) were selected as high molecular weight non-dialysable carrier molecules. *Betula alba* and *Corylus avellana* both are species of the botanical family of the Betulaceae and are known to cross-react immunologically in patients with a hypersensitivity to these spring-flowering trees. However, the HMWT-"allergens" of Corylus pollen are about 5000 times less potent on a weight basis than the pollen equivalents of Betula. A possible cause for this might be that hazelnut pollen contain a lesser quantity of reactive primary-toxic substances that could form allergens after their conjugation with carrier proteins. Therefore, it was considered feasible to reproduce HMWT-birch pollen-like allergens by interacting the Corylus proteins with the LMWT-Betula "toxins".

In a model experiment, a quantity of 10 mg of Corylus pollen HMWT preparation, isolated according to the procedure of Example I, was dissolved in 1 ml NaHCO$_3$ pH 9.5. A volume of 0.5 ml of a concentrated and unfractionated LMWT-extract of *Betula alba* pollen was then added according to the Examples I and IV. The mixture was stirred for 3 h at room temperature and was subsequently dialysed against distilled water for 18 h. In the control experiments the same amount of Corylus HMWT was diluted with 0.5 ml of water, or a dilution was made of 0.5 ml Betula LMWT in 1.0 ml of water. From these dilutions, no retentate could be obtained after dialysis. The lyophilized retentate of the Corylus HMWT/Betula LMWT reaction product was examined by spectroscopic analysis in relation to the Betula LMWT-, Betula-HMWT- and Corylus-HMWT controls.

Figure 20:
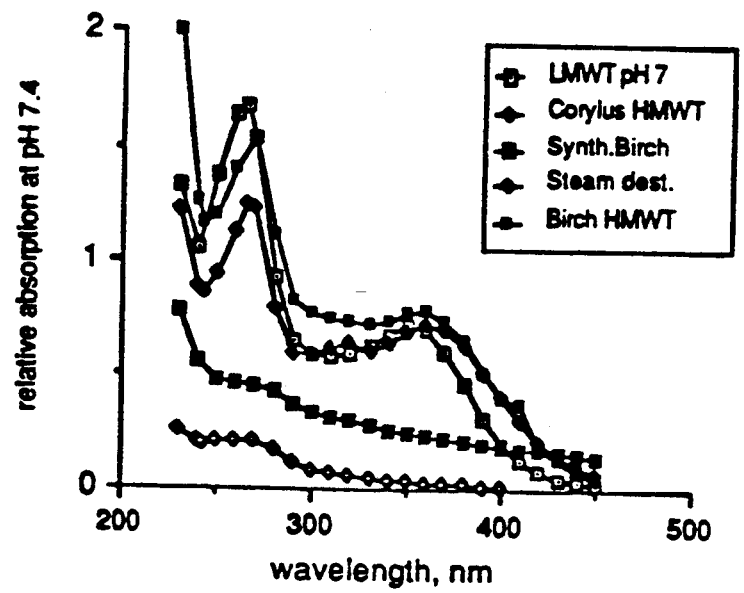

The spectroscopic data of FIG. 20 demonstrate that low molecular weight flavonoids remain strongly adsorbed to the pollen proteins and may be removed only after prolonged dialysis. As in the previous Examples, the flavonoids had no role in IgE-binding and could neither be detected in the synthetic birch allergen preparation, nor in the steam distillate of dry birch pollen. The synthetic product nontheless featured relatively strong absorption at wavelengths over 300 nm, indicating the presence of other energy-absorbing structures bound to the Corylus proteins. The results of the RAST-inhibition experiments against Betula allergens in FIG. 21 clearly show that the virtually inactive Corylus HMWT product had been converted into a high molecular antigen with the IgE-binding potential and-specificity of a birch pollen allergen: the semi-synthetic product was only 47×less potent than birch pollen HMWT and over 200×more active than the Corylus HMWT parent product.

EXAMPLE VI

A semi-synthetic product was prepared starting from Human Serum Albumin (HSA, Behringwerke AG, Germany), 0.1% w/v in 0.1M NaHCO$_3$ pH 9.4. To this solution was added an equal volume of the evaporated ethylether extract of birch pollen in 96% ethylalcohol. The suspension was agitated for 24 h on a roller bank at 20° C. and was then dialysed for 24 h from Visking membranes (nominal cut-off 10000 Daltons) against repeated changes of distilled water. The retentate was freeze dried and the resulting semi-synthetic HSA-Betula product was taken up in water to determine the UV-absorption spectrum and the RAST birch pollen-inhibitory capacity. The spectra show that chemical conjugation of the ether-soluble organic compounds as haptens had indeed occurred, as demonstrated before in Example V with Corylus HMWT. The HAS-Betula product gave 22% inhibition of birch pollen IgE-binding at a concentration of 500 µg in the test system, i.e. about 10×less potent than Corylus HMWT; unmodified HSA was completely inactive.

According to these Examples, primary-toxic compounds which can be coupled to a protein carrier in order to synthesize an allergen may be isolated directly from the ether-soluble components of pollen, or may be obtained indirectly by alkaline hydrolysis of the dialysable portion of aqueous extracts of ether-defatted pollen. Spectroscopic evidence in FIG. 22 shows that steam distillation of weakly acidic LMWT-solutions (PH 5) will also lead to identifiable compounds, although these may be structurally different as indicated by stronger carbonyl absorption at 270 nm. Finally, chemically reactive compounds may also be easily obtained by direct steam distillation of the untreated crude pollen, as illustrated in FIG. 23 for *Lolium perenne*, *Betula alba* and *Parietaria judaica*. These volatile compounds are ether-extractable from the aqueous steam distillate. FIG. 23 reproduces a few absorption spectra of such ether extracts, dried in air at room temperature and taken up in 96% ethylalcohol.

For the isolation of the volatile components from apples, a fresh sample (var. Granny Smith) was manually cut into pieces (including the skin); the seeds were removed and discarded. This fresh fruit material, 150 grams, was ground with distilled water in a Waring Blender, transferred into a round-bottom flask and submitted to steam distillation for 1 h. The aqueous distillate was extracted by shaking with diethylether. The ether layer was dried over anhydrous Na$_2$SO$_4$ and then taken to dryness in a stream of cold air. The residue was dissolved in 96% ethylalcohol and the ultraviolet absorption spectrum was recorded (FIG. 23); a separate portion was diluted with water to 50% ethanol concentration for evaluating inhibitory action on IgE-binding from human serum to birch pollen HMWT allergens. As expected, these volatile compounds (which might be terpenoids) could not inhibit IgE-binding without previous conjugation to protein carrier molecules.

The model compound protoanemonine (Carol Roth, cat. nr. 2263097) in water absorbed UV-light only in a sharp band at 215 nm; the non-volatile terpenoid compound betulinol (Carl Roth, cat. nr. 8763) in 96% ethylalcohol absorbed at 214 nm, with a shoulder at 290–300 nm. The model compound helenine (Sigman Laboratories, cat. nr. H-1375), an alantolactone, had a single absorption peak at 223 nm. Volatile mono- and sesquiterpenoids and their lactone derivatives therefore can only be detected spectroscopically in the technically cumbersome very-short-wave UV-region. FIG. 23 nevertheless shows that the volatile component(s) in the steam distillate of whole *Parietaria judaica* pollen absorbed at 227 nm, with a shoulder at 280 nm; after extracting the steam distillate with ether and passage into 96% ethylalcohol the absorption shifted to 211 nm, with a shoulder at 270 nm. An alcoholic solution of the ether-solubles from the steam distillate of crude *Lolium perenne* pollen absorbed UV-light at 213 nm with a shoulder at 268 nm. The steam distillate of birch pollen LMWT from alkaline medium (pH 10) had absorption maxima at 224 and 260–265 nm; an alcoholic solution of the ether extract absorbed at 214 nm, with a faint shoulder at 270 nm. The steam distillate of the Granny Smith apple mash absorbed at 228 nm; the ether extract in 50% ethanol absorbed both at 225 and 275 nm. These examples indicate that the water-soluble LMWT-fraction of pollen extracts contains glycosidically bound volatile terpenoids from which the primary-toxic ether-soluble aglycones may be generated by hydrolysis. The proportion of the free aglycones in commercially available pollen preparations probably is very small, because they are being eliminated by volatilzation during the customary drying process of the pollen (Guérin, B. Rev. franc Allergol 1980, 20, 193–6).

Allergenically active, usually volatile primary-toxic compounds reacting with free thiol- or amino-groups in peptides may also belong to the groups of the ortho- or para-benzoquinones, the alkyl or aryl derivatives of 1,2-dihydroxybenzene, or be reactive peroxidized lipids.

I claim:

1. A method for the separation from plant material of allergenic IgE-binding compounds for the production of IgE-binding allergens from said compounds, said compounds having a molecular weight less than 12,000 Da selected from the group consisting of terpenoids having at least one reactive carbonyl or epoxy or vinyl group and benzoquinones, comprising forming an aqueous extract of plant material containing glycosides, removing from said aqueous extract components having a molecular weight over 12,000 Da, subjecting the remaining aqueous extract containing said glycosides to hydrolysis in order to obtain a hydrolyzed material containing aglycones, isolating aglycones from said hydrolyzed material, and chemically conjugating the isolated aglycones to a carrier protein which is non-allergenic and has a molecular weight of at least 20,000 Da and which contains at least two cysteine amino acid residues to produce IgE-binding allergens.

2. The method according to claim 1, wherein said chemically conjugating step is carried out by interaction between said isolated aglycones and said protein in an aqueous medium at a temperature of 20°–40° C. and a pH value between 8.5 and 11.

* * * * *